(12) United States Patent
Kohro et al.

(10) Patent No.: US 8,252,524 B2
(45) Date of Patent: Aug. 28, 2012

(54) METHOD OF SCREENING PHARMACEUTICAL COMPOSITIONS THAT PROMOTE NUCLEAR TRANSFER OF CDC42 PROTEIN

(75) Inventors: Takahide Kohro, Tokyo (JP); Yoshikazu Shibasaki, Tokyo (JP); Takao Hamakubo, Tokyo (JP); Tatsuhiko Kodama, Tokyo (JP)

(73) Assignees: Kowa Company, Ltd., Nagoya-shi (JP); Nissan Chemical Industries, Ltd., Tokyo (JP)

( * ) Notice: Subject to any disclaimer, the term of this patent is extended or adjusted under 35 U.S.C. 154(b) by 382 days.

(21) Appl. No.: 12/548,239

(22) Filed: Aug. 26, 2009

(65) Prior Publication Data
US 2010/0221766 A1  Sep. 2, 2010

Related U.S. Application Data

(62) Division of application No. 10/590,492, filed as application No. PCT/JP2005/003008 on Feb. 24, 2005, now abandoned.

(60) Provisional application No. 60/547,075, filed on Feb. 25, 2004.

(51) Int. Cl.
*C12Q 1/00* (2006.01)
(52) U.S. Cl. ............................... 435/4; 435/18
(58) Field of Classification Search .................. None
See application file for complete search history.

(56) References Cited

U.S. PATENT DOCUMENTS

| | | |
|---|---|---|
| 3,983,140 A | 9/1976 | Endo et al. |
| 4,231,938 A | 11/1980 | Monaghan et al. |
| 4,346,227 A | 8/1982 | Terahara et al. |
| 4,444,784 A | 4/1984 | Hoffman et al. |
| 5,102,888 A | 4/1992 | Fujikawa et al. |
| 5,177,080 A | 1/1993 | Angerbauer et al. |
| 5,185,328 A | 2/1993 | Fukikawa et al. |
| 5,260,440 A | 11/1993 | Hirai et al. |
| 5,273,995 A | 12/1993 | Roth |
| 5,354,772 A | 10/1994 | Kathawala |
| 5,854,259 A | 12/1998 | Fujikawa et al. |
| 5,856,336 A | 1/1999 | Fujikawa et al. |
| 5,872,130 A | 2/1999 | Fujikawa et al. |
| 2007/0293535 A1 | 12/2007 | Kohro |

FOREIGN PATENT DOCUMENTS

| | | |
|---|---|---|
| EP | 0 304 063 A2 | 2/1989 |
| WO | 2005/079847 A1 | 9/2005 |

OTHER PUBLICATIONS

Itoh R.E. et al., Activation of Rac and Cdc42 Video Imaged by Fluorescent Resonance Energy Transfer-Based Single Molecule Probes in the Membrane of Living Cells, Molecular and Cellular Biology, Sep. 2002, vol. 22, No. 18, pp. 6582-6591.*
Murphy G.A. et al., Signaling Mediated by the Closely Related Mammalian Rho Family GTPases TC10 and Cdc42 Suggests Distinct Functional Pathways, Cell Growth & Differentiation, Mar. 2001, vol. 12, pp. 157-167.*
Etienne-Manneville S. et al., Integrin-Mediated Activation of Cdc42 Controls Cell Polarity in Migrating Astrocytes through PKC, Cell, Aug. 24, 2001, vol. 106, 489-498.*
Krall R. et al., In Vivo Rho GTPase-Activating Protein Activity of *Pseudomonas aeruginosa* Cytotoxin ExoS, Infection and Immunity, Jan. 2002, vol. 70, No. 1, pp. 360-367.*
Japanese Office Action dated Nov. 2, 2010, issued in corresponding Japanese Patent Application No. 2006-510307.
David Gregg et al., "Rac regulates cardiovascular superoxide through diverse molecular interactions: more than a binary GTP switch", Am J Physiol Cell Physiol, vol. 285 (2003) p. C723-34.
Ermond van Beek et al., "Farnesyl Pyrophosphate Synthase Is the Molecular Target of Nitrogen-Containing Bisphosphonates", Biochemical and Biophysical Research Communications, vol. 264 (1999) p. 108-11.
Louis H. Cohen et al., "Inhibitors of Prenylation of Ras and Other G-proteins and Their Application as Therapeutics", Biochemical Pharmacology, vol. 60 (2000) p. 1061-68.
Cheryl J. Hemingway et al., "Gemfibrozil activation of AMP-activated protein kinase", Biochemical Society Transactions , vol. 25 (1997) p. S676.
M. Sriram et al., "Structural Consequences of a Carcinogenic Alkylation Lesion on DNA: Effect of O6-Ethylguanine on the Molecular Structure of the d(CGC[e6G]AATTCGCG)-Netropsin Complex", Biochemistry, vol. 31 (1992) p. 11823-34.
Panos Kouklis et al., "Cdc42 Regulates the Restoration of Endothelial Barrier Function", Circulation Research, Feb. 6, 2004 p. 159-66.
Shigeru Morikawa et al., "The Effect of Statins on mRNA Levels of Genes Related to Inflammation, Coagulation, and Vascular Constriction in HUVEC", Journal of Atherosclerosis and Thrombosis, vol. 9, No. 4 (2002) p. 178-83.
Shigeru Morikawa et al., "Global Analysis of RNA Expression Profile in Human Vascular Cells Treated with Statins", Journal of Atherosclerosis and Thrombosis, vol. 11, No. 2 (2004) p. 62-72.
Huiyan Zeng et al., "Flt-1-mediated Down-regulation of Endothelial Cell Proliferation through Pertussis Toxin-sensitive G Proteins, βγ Subunits, Small GTPase CDC42, and Partly by Rac-1", The Journal of Biological Chemistry, vol. 277, No. 6 (2002) p. 4003-9.
Yuki Miyamoto et al., "Src Kinase Regulates the Activation of a Novel FGD-1-related Cdc42 Guanine Nucleotide Exchange Factor in the Signaling Pathway from the Endothelin A Receptor to JNK", The Journal of Biological Chemistry, vol. 278, No. 32 (2003) p. 29890-900.

(Continued)

*Primary Examiner* — Sandra Saucier
*Assistant Examiner* — Satyendra Singh
(74) *Attorney, Agent, or Firm* — Westerman, Hattori, Daniels & Adrian, LLP

(57) ABSTRACT

A nuclear transfer promoter for Cdc42 protein comprising an isoprenoid synthesis inhibitor and/or a geranylgeranyl transferase inhibitor such as an HMG-CoA synthase inhibitor, an HMG-CoA reductase inhibitor, an AMPK activator or a farnesyl pyrophosphoric acid synthase preparation; utilization thereof; a method therefor; a blood vessel remedy comprising the nuclear transfer promoter for Cdc42 protein as the active ingredient; and a method of screening a blood vessel remedy which comprises assaying the ability of Cdc42 protein to transfer into nucleus.

2 Claims, 1 Drawing Sheet
(1 of 1 Drawing Sheet(s) Filed in Color)

OTHER PUBLICATIONS

M.J. Lydon et al., "Vital DNA Staining and Cell Sorting by Flow Microfluorometry", Journal of Cellular Physiology, vol. 102 (1980) p. 175-81.

Beata Wójciak-Stothard et al., "Rho and Rac but not Cdc42 regulate endothelial cell permeability", Journal of Cell Science, vol. 114 (2001) p. 1343-55.

Michael D. Greenspan et al., "Inhibition of hydroxymethylglutaryl-coenzyme A synthase by L-659,699", Proc. Natl. Acad. Sci. USA, vol. 84 (1987) p. 7488-92.

Yoshimi Takai et al., "Small GTP-Binding Proteins", Physiological Reviews, vol. 81, No. 1 (2001) p. 153-208.

Yoshinari Tanaka et al., "GTP-Binding Proteins", Experimental Medical Science, vol. 21, No. 2 (2003) p. 19-26.

English translation of International Preliminary Report on Patentability for PCT/JP2005/003008 mailed on Sep. 28, 2006.

Katsuhiko Masamura et al., "Pitavastatin-Induced Thrombomodulin Expression by Endothelial Cells Acts Via Inhibition of Small G Proteins of the Rho Family", Arterioscler. Thromb. Vasc. Biol., vol. 23, No. 3, pp. 512-517 (2003).

Shigeru Morikawa et al., "The Effect of Statins on mRNA Levels of Genes Related to Inflammation, Coagulation, and Vascular Constriction in HUVEC", Human Umbilical Vein Endothelial Cells, J.Atheroscler.Thromb., vol. 9, No. 4, pp. 178-183 (2002).

Mark F. McCarty et al., "Reduction of serum C-reactive protein by statin therapy may reflect decreased isoprenylation of Rac-1, a mediator of the IL-6 signal transduction pathway", Med. Hypotheses, vol. 60, No. 5, pp. 634-639 (2003).

R.P. Brandes et al., "Withdrawal of Cerivastatin Induces Monocyte Chemoattractant Protein 1 and Tissue Factor Expression in Cultured Vascular Smooth Muscle Cells", Arterioscler.Thromb.Vasc.Biol., vol. 23, No. 10, pp. 1794-1800 (2003).

Andreas H. Wagner et al., "Improvement of Nitric Oxide-Dependent Vasodilatation by HMG-CoA Reductase Inhibitors Through Attenuation of Endothelial Superoxide Anion Formation", Arterioscler. Thromb.Vasc.Biol., vol. 20, No. 1, pp. 61-69 (2000).

Masao Takemoto et al., "Pleiotropic Effects of 3-Hydroxy-3-Methylglutaryl Coenzyme a Reductase Inhibitors", Arterioscler. Thromb.Vasc.Biol., vol. 21, No. 11, pp. 1712-1719 (2001).

Masato Eto et al., "Modulation of Coagulation and Fibrinolytic Pathways by Statins", Endothelium, vol. 10, No. 1, pp. 35-41 (2003).

Michal Mysliwiec et al., "Statin therapy—more than lipid—lowering effect", Advances in Clinical and Experimental Science, vol. 12, No. 2, pp. 185-190 (2003).

Carmine Vecchione et al., "Withdrawal of 3-Hydroxy-3-Methylglutaryl Coenzyme A Reductase Inhibitors Elicits Oxidative Stress and Induces Endothelial Dysfunction in Mice", Circulation Research, vol. 91, No. 2, pp. 173-179 (2002).

Marina Camera et al., "Cholesterol-induced Thrombogenicity of the Vessel Wall: Inhibitory Effect of Fluvastatin", Thrombosis and Haemostatis, vol. 87, No. 4, pp. 748-755 (2002).

International Search Report mailed Jun. 7, 2005 of International Application PCT/JP2005/003008.

Freshney (Culture of Animal Cells, A Manual of Basic Technique, Alan R. Liss, Inc., 1983, New York, p. 4).

Joyce, Patricia L. et al., "Rac1 and Rac3 are targets for geranylgeranyltransferase I inhibitor-mediated inhibition of signaling, transformation, and membrane ruffling," Cancer Research, Nov. 15, 2003, pp. 7959-7967, vol. 63, No. 22.

Martin, Genevieve, et al., "Statin-induced inhibition of the Rho-signaling pathway activates PPARα and induces HDL apoA-I," The Journal of Clinical Investigation, Jun. 1, 2001, pp. 1423-1432, vol. 107, No. 11.

Kajinami, Kouji, et al., "NK-104: a novel synthetic HMG-CoA reductase inhibitor," Expert Opinion on Investigational Drugs, Nov. 1, 2000, pp. 2653-2661, vol. 9, No. 11.

Flores, Nicholas A., "Pitavastatin Nissan/Kowa Yakuhin/Novartis/Sankyo," Current Opinion in Investigational Drugs, Pharmapress, US, Sep. 1, 2002, pp. 1334-1341, vol. 3, No. 9.

Keller, Patricia J., et al., "Visual monitoring of post-translational lipid modifications using EGFP-GTPase probes in live cells," Methods: A Companion to Methods in Enzymology, Oct. 1, 2005, pp. 131-137, vol. 37, No. 2.

Supplemental European Search Report dated Aug. 28, 2009 issued in corresponding European Patent Application 05719458.

Dermer, Gerald B.; "Another Anniversary for the War on Cancer"; Bio/Technology; vol. 12, Mar. 1994; p. 230.

Gura, Trisha; "Systems for Identifying New Drugs Are Often Faulty"; Science; vol. 278, 1997; pp. 1041-1042.

Lefer, Allen M. et al.; "Vascular Effects of HMG Co-A-reductase inhibitors (statins) unrelated to cholesterol lowering: new concepts for cardiovascular disease"; Cardiovascular Research; vol. 49, 2001; pp. 281-287.

* cited by examiner

METHOD OF SCREENING PHARMACEUTICAL COMPOSITIONS THAT PROMOTE NUCLEAR TRANSFER OF CDC42 PROTEIN

RELATED APPLICATION

This application is a divisional application of U.S. patent application Ser. No. 10/590,492 filed on Aug. 24, 2006, which is a national stage application of international application No. PCT/JP2005/003008, filed Feb. 24, 2005, which claims benefit of U.S. Provisional Application No. 60/547,075, filed on Feb. 25, 2004, the entire contents of which are incorporated herein by reference.

TECHNICAL FIELD

The present invention is based on a finding that an isoprenoid synthesis inhibitor and/or a geranylgeranyl transferase inhibitor, particularly an HMG-CoA reductase inhibitor that is an isoprenoid synthase inhibitor has an action of promoting the transfer of Cdc42 protein into a nucleus. That is, the present invention relates to a nuclear transfer promoter for Cdc42 protein comprising an isoprenoid synthesis inhibitor and/or a geranylgeranyl transferase inhibitor, preferably an isoprenoid synthesis inhibitor, more preferably an HMG-CoA reductase inhibitor, use of the inhibitor as a nuclear transfer promoter, a method of promoting the transfer of Cdc42 protein into a nucleus by using the inhibitor, and a pharmaceutical composition including the inhibitor. Further, the present invention relates to a blood vessel remedy including the nuclear transfer promoter for Cdc42 protein as the active ingredient, and a method of screening a blood vessel remedy which comprises assaying the ability of Cdc42 protein to transfer into a nucleus.

BACKGROUND ART

GTP-binding protein (G protein) is a generic name of endogenous protein group having an activity of hydrolyzing GTP, and has been known for a G protein group involved in mRNA translation, a trimer G protein group conjugated with 7-times transmembrane receptor, a low-molecular-weight G protein group ("Experimental Medicine", 21:137-145, 2003) and the like. Among these groups, 100 or more kinds of low-molecular-weight G protein proteins have been reported as proteins having molecular weights of 20,000 to 30,000 with no subunit structure, and after isoprenylation, these proteins transfer to cell membranes to participate in intracellular signal transmission as GTP-bound form (on)/GDP-bound form (off).

The low-molecular-weight G protein group is further divided into five super-families, that is, Ras, Rho, Rab, Arf and Ran (Physiol. Rev., 81:153-208, 2001). Among these families, the Rho family is further divided into subfamilies such as Rho, Rac, Cdc42. The Rho family regulates cellular functions via re-organization of an actin cytoskeleton, and similarly to the Ras family, participates in gene expression. Rho induces formation of actin stress fiber or focal contact, Rac induces formation of lamellipodia, and Cdc42 induces formation of filopodia.

Cdc42 that is a low-molecular-weight G protein belonging to the Rho family is a protein having a molecular weight of 21 kDa and participating in various cellular activities such as filopodia formation, cellular adhesion, cellular motility, cellular polarity, and gene expression. Cdc 42 target protein which is the GTP-bound activated type has been known for PAK (p21-activated kinase), MRCK (myotonic dystrophy kinase-related Cdc42 binding kinase), WAPS, and IQGAP1. That is, Cdc42 regulates the expression of various genes via MAP kinase cascade by activation of PAK, and in connection with WASP and MRCK, participates in formation of focal contact and filopodia, or in connection with IQGAP1, regulates intercellular adhesion.

On one hand, an HMG-CoA (3-hydroxy-3-methyl-glutaryl-CoA) reductase inhibitor is an inhibitor of an enzyme catalyzing conversion of HMG-CoA into mevalonic acid in an early rate-determining stage in biosynthesis of cholesterol, and is known as a hypercholesterolemia remedy. The HMG-CoA reductase inhibitor has been verified to reduce the onset of arteriosclerosis in a large-scale test, and from overlap analysis or the like, it has been revealed that this reduction of the onset is responsible for HMG-CoA reductase inhibitor's action in a vascular wall, aside from its action of reducing cholesterol by inhibiting HMG-CoA reductase in the liver.

That is, it is believed that the HMG-CoA reductase inhibitor inhibits HMG-CoA reductase in cells of a vascular wall, and via its action of reducing the formation of isoprenoid, reduces the activity of low-molecular-weight G protein, thus exerting various influences on cellular functions to exhibit anti-inflammatory reaction in the vascular wall thereby suppressing arteriosclerosis.

Further, the HMG-CoA reductase inhibitor has actions such as suppression of endothelial cell activation, improvement of endothelial functions, suppression or improvement of adhesion or foaming of monocytes/macrophages, suppression of migration/proliferation of smooth muscles, and stabilization of plaques, and Rho, Rae, and Cdc42 that are low-molecular-weight G proteins in the Rho subfamily are reported to participate in these actions. Particularly, the effect of the HMG-CoA reductase inhibitor on improvement of endothelial functions appears evidently in a short time after administration, and is considered important among the various actions.

Recently, it is revealed that Rac participates in signal transmission mediated by angiotensin II, PDGF, thrombin, endothelin, leukotriene B4 and the like in vascular walls and promotes the activity of NADPH, thus playing an important role in the progress of a vascular disease (Am. J. Physiol. Cell Physiol., 285:C723-734, 2003), and it is reported that Cdc42 also participates in proliferation of vascular endothelial cells and in recovery of barrier functions (J. Cell Sci., 114:1343-55, 2001; J. Biol. Chem., 277:4003-9., 2002; Circ. Res., 94:159-166, 2004) and also in signal transmission of endothelin (J. Biol. Chem., 278:29890-900, 2003).

Further, the present inventors examined the influence of pitavastatin as HMG-CoA reductase inhibitor on gene expression in vascular endothelial cells, and they found that pitavastatin suppresses expression of inflammatory cytokine IL-8 or MCP-1, expression of endothelin and expression of PAI-1, promotes expression of NO synthase involved in vascular expansion and shrinkage, expression of thrombomodulin in a coagulation and fibrinolysis system (J. Atheroscler. Thromb., 9:178-183, 2002), and suppresses expression of PTX3 (promoting expression of TF and serving as an indicator of progress of arteriosclerosis) (J. Atheroscler. Thromb., 11:62-183, 2004).

DISCLOSURE OF INVENTION

As a result of eager study, the present inventors surprisingly found that Rac and Cdc42 were transferred to nuclei by treatment with an isoprenoid synthesis inhibitor and/or a geranylgeranyl transferase inhibitor, particularly by treatment with an HMG-CoA reductase inhibitor, and the present invention was thereby completed.

That is, the present invention relates to a nuclear transfer promoter for Cdc42 protein comprising an isoprenoid synthesis inhibitor and/or a geranylgeranyl transferase inhibitor, preferably an isoprenoid synthesis inhibitor, more preferably one kind of isoprenoid synthesis inhibitor, that is, an HMG-CoA reductase inhibitor.

The present invention also relates to use, as a nuclear transfer promoter for Cdc42 protein, of an isoprenoid synthesis inhibitor and/or a geranylgeranyl transferase inhibitor, preferably an isoprenoid synthesis inhibitor, more preferably one kind of isoprenoid synthesis inhibitor, that is, an HMG-CoA reductase inhibitor, and provides a method of promoting the transfer of Cdc42 protein into a nucleus, which includes administering an isoprenoid synthesis inhibitor and/or a geranylgeranyl transferase inhibitor to a cell.

Further, the present invention provides a blood vessel remedy including the nuclear transfer promoter for Cdc42 protein as the active ingredient, as well as a pharmaceutical composition for vascular treatment comprising the nuclear transfer promoter for Cdc42 protein and a pharmaceutically acceptable carrier.

Further, the present invention provides use of the nuclear transfer promoter for Cdc42 protein in producing a blood vessel remedy, as well as a therapeutic/prevention method for vascular disorders including administering the nuclear transfer promoter for Cdc42 protein in an effective amount for therapy/prevention to a patient in need of therapy/prevention of vascular disorders.

Further, the present invention provides a method of screening a blood vessel remedy, which includes measuring the transfer of Cdc42 protein into a nucleus. Specifically, the present invention provides a method of screening a blood vessel remedy, which includes adding a test substance to a Cdc42 protein-expressing cell and measuring the transfer of Cdc42 protein into the nucleus.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

The present inventors measured the behavior of Cdc42 protein in HUVEC with an HMG-CoA reductase inhibitor, particularly pitavastatin. For this measurement, a gene encoding a Cdc42/fluorescence protein GFP fusion protein was introduced into HUVEC to prepare a transformed cell expressing a GFP/Cdc42 fusion protein. This transformed cell was cultured, and the state of Cdc42 distributed in the cell in the presence or absence of pitavastatin was examined by observing the fluorescence of GFP. These results are shown in FIGS. 1 to 3.

Figure 1:
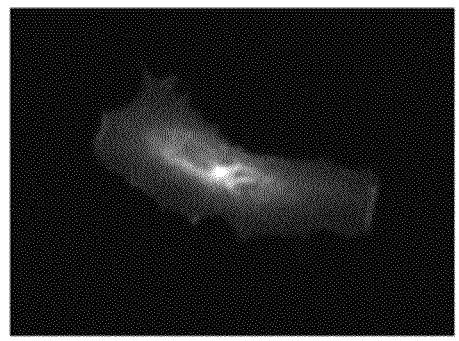
FIG. 1 is a photograph, under a fluorescence microscope, of transformed cells which were introduced a gene encoding a green fluorescence protein (GFP)/Cdc42 fusion protein, and were cultured in the absence of pitavastatin.

FIG. 1 is a photograph substituted for a drawing, showing the result of observation, under a fluorescence microscope, of the state of Cdc42 distributed in the transformed cells which has been cultured in the absence of pitavastatin. In FIG. 1, the fluorescence of GFP can be observed in the nearly whole area of the cells, thus revealing that Cdc42 protein region is distributed in the whole area of the transformed cells.

Figure 2:
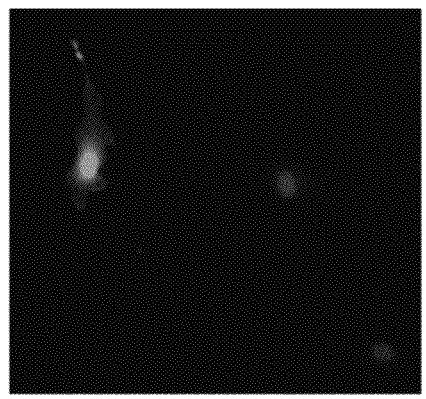
FIG. 2 is a photograph, under a fluorescence microscope, of transformed cells which were introduced a gene encoding GFP/Cdc42 fusion protein, and were cultured in the presence of pitavastatin.
Figure 3:
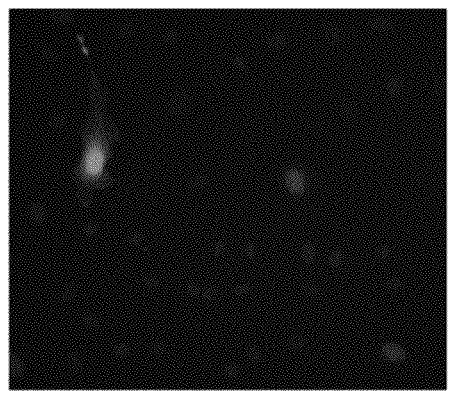
FIG. 3 is a photograph, under a fluorescence microscope, of transformed cells whose nuclei were stained (red) by adding nucleus-staining dye Hoechst after introduction of a gene encoding GFP/Cdc42 fusion protein and cultivation in the presence of pitavastatin.

FIG. 2 is a photograph substituted for a drawing, showing the result of observation, under a fluorescence microscope, of the state of Cdc42 distributed in the transformed cells which has been cultured in the presence of pitavastatin. In FIG. 2, it can be observed that the fluorescence of GFP was localized in a certain area of the cells. For further confirming the position at which Cdc42 is localized in the cells, the cells were stained with Hoechst (Lydon M., et al., J. Cell Physiol., 102, 175-181 (1980); Sriram M., et al., Biochemistry, 31, 11823-11834 (1992)), and FIG. 3 is a photograph substituted for a drawing, showing the result of this staining. In FIG. 3, the nuclei stained with Hoechst are observed to be red, and this corresponded to the site at which the fluoresce of GFP is localized.

Hoechst used herein is a fluorescent dye having an ability to permeate through a cell membrane and binding specifically to an AT sequence in a minor groove of DNA. From the above experiment, it has been revealed that upon treatment of the vascular endothelial cells with pitavastatin, GFP-Cdc42 is transferred to a nucleus, that is, to the same position as the site stained with the nucleus-staining dye Hoechst. It has been thus revealed that the HMG-CoA reductase inhibitor has an action of allowing Cdc42 protein in the cell to transfer into the nucleus.

The nuclear transfer promoter for Cdc42 protein according to the present invention exerts an important influence on the actions in which Cdc42 protein is involved, such as regulation of cellular motility, cellular polarity, intracellular signal transmission and gene expression, particularly on regulation of gene expression in vascular wall cells, and is considered useful as a blood vessel remedy, particularly an endothelial cell function improver and a cell adhesion inhibitor.

The isoprenoid synthesis inhibitor as the nuclear transfer promoter for Cdc42 protein according to the present invention can include HMG-CoA synthase inhibitors (Proc. Natl. Acad. Sci. USA., 84:7488-92, 1987), HMG-CoA reductase inhibitors, AMPK activators such as fibrate (Biochem. Soc. Trans., 25:S676, 1997), and farnesylpyrophosphoric acid synthase inhibitors such as N-containing bisphosphonate. (Biochem. Biophys. Res. Commun., 264:108-111, 1999). The geranylgeranyl transferase inhibitor as the nuclear transfer promoter for Cdc42 protein according to the present invention can include inhibitors described in known literatures, for example Biochemical Pharmacology, 60:1061-1068, 2000. These enzyme inhibitors may be any inhibitors capable of completely or partially inhibiting the activity of the objective enzyme.

Specifically, the following compounds can be mentioned.

Lovastatin (chemical name: (+)-(1S,3R,7S,8S,8aR)-1,2,3,7,8,8a-hexahydro-3,7-dimethyl-8-[2-[(2R,4R)-tetrahydro-4-hydroxy-6-oxo-2H-pyran-2-yl]ethyl]-1-naphthyl (S)-2-methyl butyrate (see U.S. Pat. No. 4,231,938));

Simvastatin (chemical name: (+)-(1S,3R,7S,8S,8aR)-1,2,3,7,8,8a-hexahydro-3,7-dimethyl-8-[2-[(2R,4R)-tetrahydro-4-hydroxy-6-oxo-2H-pyran-2-yl]ethyl]-1-naphthyl 2,2-dimethyl butanoate (see U.S. Pat. No. 4,444,784));

Pravastatin (chemical name: (+)-(3R,5R)-3,5-dihydroxy-7-[(1S,2S,6S,8S,8aR)-6-hydroxy-2-methyl-8-[(S)-2-methylbutyryloxy]-1,2,6,7,8,8a-hexahydro-1-naphthyl] heptenoic acid (see U.S. Pat. No. 4,346,227));

Fluvastatin (chemical name: (3RS,5SR,6E)-7-[3-(4-fluorophenyl)-1-(1-methylethyl)-1H-ind ol-2-yl]-3,5-dihydroxy-6-heptenoic acid (see U.S. Pat. No. 5,354,772));

Atorvastatin (chemical name: (3R,5R)-7-[2-(4-fluorophenyl)-5-isopropyl-3-phenyl-4-phenyl carbamoyl-1H-pyrol-1-yl]-3,5-dihydroxyheptanoic acid (see U.S. Pat. No. 5,273, 995));

Cerivastatin (chemical name: (3R,5S)-erythro-(E)-7-[4-(4-fluorophenyl)-2,6-diisopropyl-5-methoxymethyl-pyridin-3-yl]-3,5-dihydroxy-6-heptenoic acid (see U.S. Pat. No. 5,177,080));

Mevastatin (chemical name: (+)-(1S,3R,7S,8S,8aR)-1,2,3,7,8,8a-hexahydro-7-methyl-8-[2-[(2R,4R)-tetrahydro-4-hydroxy-6-oxo-2H-pyran-2-yl]ethyl]-1-naphthyl (S)-2-methyl butyrate (see U.S. Pat. No. 3,983,140));

Rosuvastatin (chemical name: 7-[4-(4-fluorophenyl)-6-isopropyl-2-(N-methyl-N-methane sulfonylaminopyridine)-5-yl]-(3R,5S)-dihydroxy-(E)-6-heptenoic acid (see U.S. Pat. No. 5,260,440 and Japanese Patent No. 2,648,897)); and Pitavastatin ((3R,5S,6E)-7-[2-cylopropyl-4-(4-fluorophenyl)-3-quinolyl]-3,5-dihydroxy-6-heptenoic acid (see U.S. Pat. No. 5,856,336 and Japanese Patent No. 2,569,746)).

If pharmaceutically necessary, the inhibitor can be used as a salt or solvate. Particularly preferable inhibitor is pitavastatin.

In another aspect of the present invention, the method of screening a blood vessel remedy, which includes measuring the transfer of Cdc42 protein into the nucleus includes a method of labeling or staining Cdc42 protein and identifying the transfer thereof into the nucleus. The method of labeling Cdc42 protein includes genetic engineering techniques. Specific examples include method of utilizing the fusion protein of fluorescence proteins BET, CFP and YET, including GET (Atsushi Miyawaki: Intracellular phenomenon is visualized by fluorescence bio-imaging. Riken News 255, September 2002) and Cdc42 protein. The method of staining Cdc42 protein includes immunological techniques. Specifically, use of a fluorescence antibody or enzyme antibody can be mentioned. The method is particularly preferably a method which involves preparing a fusion protein of a fluorescence protein such as GFP and Cdc42 protein and then visually identifying the transfer of the fusion protein into the nucleus.

The nuclear transfer promoter for Cdc42 protein according to the present invention can be used not only as a pharmaceutical preparation in therapy/prevention of vascular disorders, but also as a reagent for localizing Cdc42 protein in cellular nuclei in a test using various cells. That is, the nuclear transfer promoter can be used not only as the active ingredient in a pharmaceutical preparation but also as an experimental reagent or a reagent in a diagnostic medicine.

The blood vessel remedy of the present invention includes a pharmaceutical composition for vascular treatment, which uses the nuclear transfer promoter for Cdc42 protein according to the present invention or is made of the nuclear transfer promoter and a pharmaceutically acceptable carrier.

The route of administration of the blood vessel remedy of the present invention includes, for example, oral administration by tablets, capsules, granules, powders, syrups or the like and parenteral administrations by intravenous injections, intramuscular injections, suppositories, inhalations, transdermal absorbers, eye-drops, nasal agents or the like.

For preparing the pharmaceutical preparation in such various forms, the active ingredient is used alone or in suitable combination with other pharmaceutically acceptable one or more additives such as excipient, binder, extender, disintegrating agent, surfactant, lubricant, dispersant, buffer agent, preservative, taste corrective, flavoring, coating agent, carrier, diluent or the like.

Particularly, the route of administration of the HMG-CoA reductase inhibitor is preferably oral administration. For preparation of the pharmaceutical preparation for oral administration, the pH of the preparation is regulated in consideration of the stability of the active ingredient (Japanese Patent Application Laid-open No. 2-6406, Japanese Patent No. 2,774,073, and WO97/23200, the disclosure of which is incorporated by reference herein).

The amount of the pharmaceutical preparation administered varies depending on the weight, age, sex and symptoms of the patient, and in the case of an adult, it is usually preferable that the isoprenoid synthesis inhibitor and/or the geranylgeranyl transferase inhibitor as the active ingredient is administered orally in a daily dose of 0.01 to 1000 mg, particularly 0.1 to 100 mg, all at once or in divided portions.

EXAMPLE

Hereinafter, the present invention is described in more detail by referenced to the Examples, but the present invention is not limited to the Example.

Example 1

A gene encoding the whole area of a Cdc42 translation region was introduced into a predetermined position of a commercial plasmid pEGFP-C1 for preparation of a fusion protein consisting of GFP and a desired protein, to construct a plasmid comprising the GFP-Cdc42 gene.

After 1×10 HUVECs were put to a 6-well plate and then cultured overnight in EGM-2 medium. Using Fugene 6, the plasmid construct DNA prepared above was added in an amount of 0.8 μg/well to the cells. The cells were further cultured for 21 hours in EGM-2 medium, and then the fluorescence of GFP was observed under a fluorescence microscope. The result of this observation is shown in FIG. 1.

Six hours after the culture of HUVECs to which the plasmid construct DNA had been added was initiated, pitavastatin was added to the cells to a final concentration of 1 μM. And then the cells were subjected to stationary culture for 15 hours, fixed onto a prepared slide and observed under a fluorescence microscope. The result of this observation is shown in FIG. 2. Further, the cells were stained with the nucleus-staining dye Hoechst. The result of this staining is shown in FIG. 3.

Industrial Applicability

The present invention relates to a nuclear transfer promoter for Cdc42 protein, and Cdc42 protein is known to participate in proliferation of vascular endothelial cells, in recovery of barrier functions, and in signal transmission of endothelin and plays an important role in the progress of vascular diseases via participation in regulating the expression of various genes involved in vascular shrinkage/expansion, inflammations, and blood coagulation/fibrinolysis, and thus the medicine of the present invention is industrially extremely useful as a pharmaceutical preparation for treatment and prevention of various vascular diseases.

In addition, the present invention provides a method of screening a blood vessel remedy which includes measuring the transfer of Cdc42 protein to the nucleus, and is industrially useful as a means for developing new therapeutic agents and prevention agents for vascular diseases.

The invention claimed is:

1. A method of screening for a pharmaceutical composition for treatment of arteriosclerosis, comprising:

adding a test substance to a first human umbilical vein endothelial cells (HUVECs) culture which comprises HUVECs expressing Cdc42 fusion protein comprising a fluorescent protein, culturing a second HUVECs culture which comprises HUVECs expressing the Cdc42 fusion protein comprising the fluorescent protein, culturing said first and second HUVECs culture for a sufficient time for the fluorescent Cdc42 fusion protein to transfer into the nucleus, said first HUVECs culture being cultured in the presence of the test substance and said second HUVECs culture being cultured in the absence of the test substance, measuring distribution of the amount of fluorescence in said first HUVECs culture and said second HUVECs culture, and determining, if the distribution of fluorescence in the nucleus of said first HUVECs culture is greater than the distribution of fluorescence in the nucleus of said second HUVECs culture, thereby identifying a pharmaceutical composition suitable for the treatment of arteriosclerosis.

2. The screening method according to claim 1, wherein said first and second HUVECs culture are cultured for 15 hours prior to said measuring distribution of the amount of fluorescence in said first and second HUVECs cultures.

* * * * *